United States Patent
Star-Lack et al.

(10) Patent No.: US 10,342,504 B2
(45) Date of Patent: Jul. 9, 2019

(54) METHODS AND SYSTEMS FOR ESTIMATING SCATTER

(71) Applicant: VARIAN MEDICAL SYSTEMS, INC., Palo Alto, CA (US)

(72) Inventors: Josh Star-Lack, Palo Alto, CA (US); Mingshan Sun, Menlo Park, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 60 days.

(21) Appl. No.: 15/023,396

(22) PCT Filed: Sep. 25, 2014

(86) PCT No.: PCT/US2014/057552
§ 371 (c)(1),
(2) Date: Mar. 20, 2016

(87) PCT Pub. No.: WO2015/048350
PCT Pub. Date: Apr. 2, 2015

(65) Prior Publication Data
US 2016/0213345 A1 Jul. 28, 2016

Related U.S. Application Data

(60) Provisional application No. 61/882,566, filed on Sep. 25, 2013.

(51) Int. Cl.
*G06K 9/00* (2006.01)
*A61B 6/00* (2006.01)
(Continued)

(52) U.S. Cl.
CPC ............ *A61B 6/5282* (2013.01); *A61B 6/032* (2013.01); *A61B 6/5205* (2013.01);
(Continued)

(58) Field of Classification Search
CPC ..... A61B 6/032; A61B 6/5205; A61B 6/5282; G01N 2223/1016; G01N 2223/419;
(Continued)

(56) References Cited

U.S. PATENT DOCUMENTS 5,666,391 A    9/1997 Ohnesorge et al.
6,490,476 B1   12/2002 Townsend et al.
(Continued)

FOREIGN PATENT DOCUMENTS

JP    2012250043 A    12/2012
WO    2013/192600 A1  12/2013

OTHER PUBLICATIONS

Mainegra-Hing, Ernesto, and Iwan Kawrakow. "Fast Monte Carlo calculation of scatter corrections for CBCT images." Journal of Physics: Conference Series. vol. 102. No. 1. IOP Publishing, 2008.*
(Continued)

*Primary Examiner* — Nirav G Patel
(74) *Attorney, Agent, or Firm* — SU IP Consulting

(57) ABSTRACT

One example method for estimating scatter associated with a target object may include acquiring a set of original projection data that includes primary radiation and scattered radiation at one or more selected projection angles associated with the target object, generating a first set of estimated scatter data from the set of original projection data, generating reconstructed image data by performing a first pass reconstruction using the first set of estimated scatter data, and generating a set of reference scatter data associated with the target based on the reconstructed image data. The example method may also include generating a set of reference primary plus scatter data associated with the target object based on the reconstructed image data, generating a second set of estimated scatter data associated with the target object based on the set of reference primary plus scatter data,
(Continued)

and generating perturbation data associated with the target object.

20 Claims, 9 Drawing Sheets

(51) Int. Cl.
| | |
|---|---|
| *A61B 6/03* | (2006.01) |
| *G01N 23/046* | (2018.01) |
| *G06T 7/00* | (2017.01) |
| *G06T 11/00* | (2006.01) |

(52) U.S. Cl.
CPC ......... *G01N 23/046* (2013.01); *G06T 7/0012* (2013.01); *G06T 11/003* (2013.01); *G01N 2223/1016* (2013.01); *G01N 2223/419* (2013.01); *G06T 2207/10081* (2013.01)

(58) Field of Classification Search
CPC ................ G01N 23/046; G06T 11/003; G06T 2207/10081; G06T 7/0012
See application file for complete search history.

(56) References Cited

U.S. PATENT DOCUMENTS

| | | |
|---|---|---|
| 6,687,326 B1 | 2/2004 | Bechwati et al. |
| 7,336,760 B2 | 2/2008 | Virshup et al. |
| 8,199,873 B2 | 6/2012 | Star-Lack et al. |
| 8,326,011 B2 | 12/2012 | Star-Lack et al. |
| 8,649,587 B2 | 2/2014 | Star-Lack et al. |
| 8,682,055 B2 | 3/2014 | Star-Lack et al. |
| 8,705,827 B2 | 4/2014 | Zhu et al. |
| 8,897,527 B2 | 11/2014 | Star-Lack et al. |
| 8,989,469 B2 | 3/2015 | Fahimian et al. |
| 9,330,458 B2 | 5/2016 | Star-Lack et al. |
| 2002/0048339 A1 | 4/2002 | Schneider et al. |
| 2003/0147491 A1 | 8/2003 | Gonzalez Trotter et al. |
| 2003/0215057 A1 | 11/2003 | Trotter et al. |
| 2004/0190679 A1 | 9/2004 | Waggener et al. |
| 2006/0088140 A1 | 4/2006 | Fahrig et al. |
| 2007/0189440 A1 | 8/2007 | Rinkel et al. |
| 2008/0013693 A1 | 1/2008 | Kusch et al. |
| 2008/0253515 A1 | 10/2008 | Bertram et al. |
| 2008/0304620 A1 | 12/2008 | Karellas |
| 2009/0202127 A1 | 8/2009 | Bertram et al. |
| 2009/0290682 A1 | 11/2009 | Star-Lack et al. |
| 2010/0046696 A1 | 2/2010 | Maltz |
| 2011/0255655 A1 | 10/2011 | Star-Lack et al. |
| 2011/0255656 A1 | 10/2011 | Star-Lack et al. |
| 2012/0314921 A1 | 12/2012 | Star-Lack et al. |

OTHER PUBLICATIONS

Maltz, Jonathan S., et al. "Focused beam-stop array for the measurement of scatter in megavoltage portal and cone beam CT imaging." Medical physics 35.6 (2008): 2452-2462.*

The Extended European Search Report, EP 14848042.9, dated May 9, 2017.
Josh Star-Lack et al., "Scatter Correction with Kernel Perturbation", Proceedings of SPIE, Mar. 6, 2013, pp. 86681I, vol. 8668.
International Preliminary Report on Patentability, International application No. PCT/US2014/057552, dated Mar. 29, 2016.
International Search Report and Written Opinion of the International Searching Authority, International application No. PCT/US2013/047199, dated Nov. 12, 2013.
Atila Ersahin et al., "A Digital Filtration Technique for Scatter-Glare Correction Based on Thickness Estimation", IEEE Transactions on Medical Imaging, Sep. 1995, pp. 587-595, vol. 14, No. 3.
L Alan Love et al., "Scatter Estimation for a Digital Radiographic System Using Convolution Filtering", Med. Phys., Mar./Apr. 1987, pp. 178-185, vol. 14, No. 2.
J Maltz et al., "Unified Algorithm for KV and MV Scatter and Beam-Hardening Correction Using the Convolution-Superposition Method", Medical Physics, Jun. 2006, p. 2280, vol. 33, No. 6.
B. Ohnesorge et al., "Efficient Object Scatter Correction Algorithm for Third and Fourth Generation CT Scanners", European Radiology, 1999, pp. 563-569, vol. 9.
J.H. Siewerdsen et al., "Cone-Beam Computed Tomography with a Flat-Panel Imager: Magnitude and Effects of X-Ray Scatter", Medical Physics, Feb. 2001, pp. 220-231, vol. 28, No. 2.
J.H. Siewerdsen et al., "A Simple, Direct Method for X-Ray Scatter Estimation and Correction in Digital Radiography and Cone-Beam CT", Medical Physics, Jan. 2006, pp. 187-197, vol. 33, No. 1.
Roland E. Suri et al., "Comparison of Scatter Correction Methods for CBCT", Proceedings of SPIE, 2006, pp. 614238-1-614238-10, vol. 6142.
G. Virshup et al., "Scatter Characterization in Cone-Beam CT Systems with Offset Flat Panel Imagers", Medical Physics, Jun. 2006, p. 2288, vol. 33, No. 6.
M. Zellerhoff et al., "Low Contrast 3D-Reconstruction from C-Arm Data", Proceedings of SPIE, 2005, pp. 646-655, vol. 5745.
Lei Zhu et al., "Scatter Correction Method for X-Ray CT Using Primary Modulation: Theory and Preliminary Results", IEEE Transactions on Medical Imaging, 2006, pp. 1573-1587, vol. 25, No. 12.
Schmidtlein et al., "Validation of Gate Monte Carlo Simulations of the GE Advance/ Discovery LS PET Scanners", 2006, Medical Physics, pp. 198-208, vol. 33, No. 1.
Reitz, Development and Evaluation of a Method for Scatter Correction in KV Cone Beam Computer Tomography, Apr. 30, 2008, Doctoral Dissertation, Ruperto-Carola University of Heidelberg, Germany.
Atherton et al., "CT Doses in Cylindrical Phantoms", Physics in Medicine and Biology, 1995, pp. 891-911, vol. 40.
Jarry et al., "A Monte Carlo-based Method to Estimate Radiation Dose from Spiral CT: from Phantom Testing to Patient-Specific Models", Physics in Medicine and Biology, 2003, pp. 2645-2663.
Josh Star-Lack et al., "Scatter Correction for the On-Board Imager Using a Kernel Model", Medical Physics, Jun. 2007, p. 2342, vol. 34, No. 6, Abstract No. SU-FF-I-19.
Josh Star-Lack et al., "Efficient Scatter Correction Using Asymmetric Kernels", Medical Imaging 2009, Proceeding of SPIE, Feb. 9, 2009, pp. 1Z-1 to 1Z-12, vol. 7258.

* cited by examiner

FIG. 8A
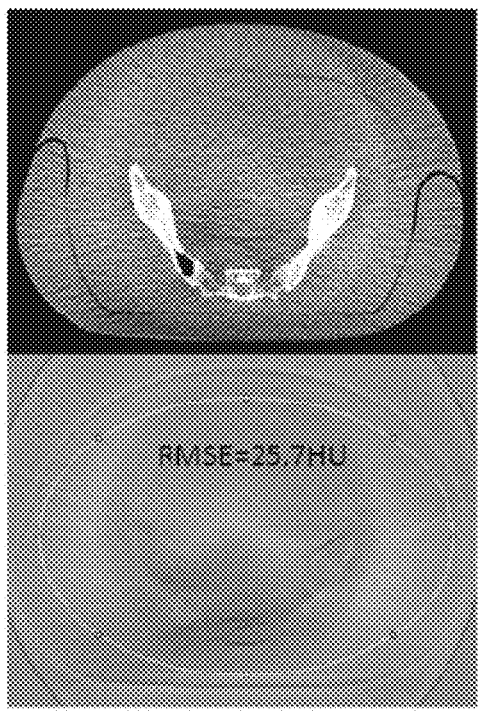
FIG. 8B
FIG. 8C
FIG. 8D

METHODS AND SYSTEMS FOR ESTIMATING SCATTER

CROSS-REFERENCE TO RELATED APPLICATIONS

This present application is a U.S. national stage filing under 35 U.S.C. § 371 of International Application No. PCT/US2014/057552, which claims the benefit of the U.S. Provisional Application No. 61/882,566, filed on Sep. 25, 2013. This application is also related to commonly owned U.S. Provisional Application No. 61/663,494 (filed on Jun. 22, 2012) and International Application No. PCT/US2013/047199 (filed on Jun. 22, 2013). The U.S. Provisional Application No. 61/882,566 and the International Application No. PCT/US2014/057552, including any appendices or attachments thereof, are hereby incorporated by reference in their entirety.

BACKGROUND

Unless otherwise indicated herein, the approaches described in this section are not prior art to the claims in this application and are not admitted to be prior art by inclusion in this section.

Computerized tomography (CT) involves the imaging of the internal structure of a target object by collecting several projection images ("radiographic projections") in a single scan operation ("scan"), and is widely used in the medical field to view the internal structure of selected portions of the human body. In an ideal imaging system, rays of radiation travel along respective straight-line transmission paths from the radiation source, through a target object, and then to respective pixel detectors of the imaging system without generating scattered rays. However, in real systems, when a quantum of radiation is absorbed by a portion of the target object, one or more scattered rays that deviate from the transmission path of the incident radiation are often generated. These scattered rays are often received by "surrounding" detector elements that are not located on the transmission path that the initial quantum of radiation was transmitted on, thereby creating measurement errors.

The measurement errors created by scattered radiation cause artifacts and loss of spatial and contrast resolution in the radiographic projection data and the CT images produced by the imaging system. The scattered radiation can also cause numerical errors in image reconstruction algorithms. All of the foregoing leads to image degradation.

Solutions have been proposed to estimate and/or correct scattered radiation. For solutions that use scatter kernels, certain scatter resulting from internal inhomogeneities or external adjacent objects may be difficult to model. Other solutions that include comparing estimated scatter from projection data with simulated scatter may need to address the difficult process of scaling the simulation profile.

Accordingly, there is a need to develop techniques that can further improve the estimation accuracy but in an efficient manner.

SUMMARY

In accordance with at least some embodiments of the present disclosure, a method for estimating scatter associated with a target object is disclosed. The method may include acquiring, using a radiation source and a detector of an imaging system, a set of original projection data that includes primary radiation and scattered radiation at one or more selected projection angles associated with the target object, generating a first set of estimated scatter data from the set of original projection data using a scatter estimation algorithm, generating reconstructed image data by performing a first pass reconstruction using the first set of estimated scatter data. generating a set of reference scatter data associated with the target object at the one or more selected projection angles based on the reconstructed image data, generating a set of reference primary plus scatter data associated with the target object at the one or more selected projection angles based on the reconstructed image data, generating a second set of estimated scatter data associated with the target object based on the set of reference primary plus scatter data using the scatter estimation algorithm, and generating perturbation data associated with the target object by comparing the reference scatter data with the second set of estimated scatter data.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 8A, FIG. 8B, FIG. 8C and FIG. 8D are reconstructed images of a large pelvis phantom scanned using an imaging system;

DETAILED DESCRIPTION

Figure 1:
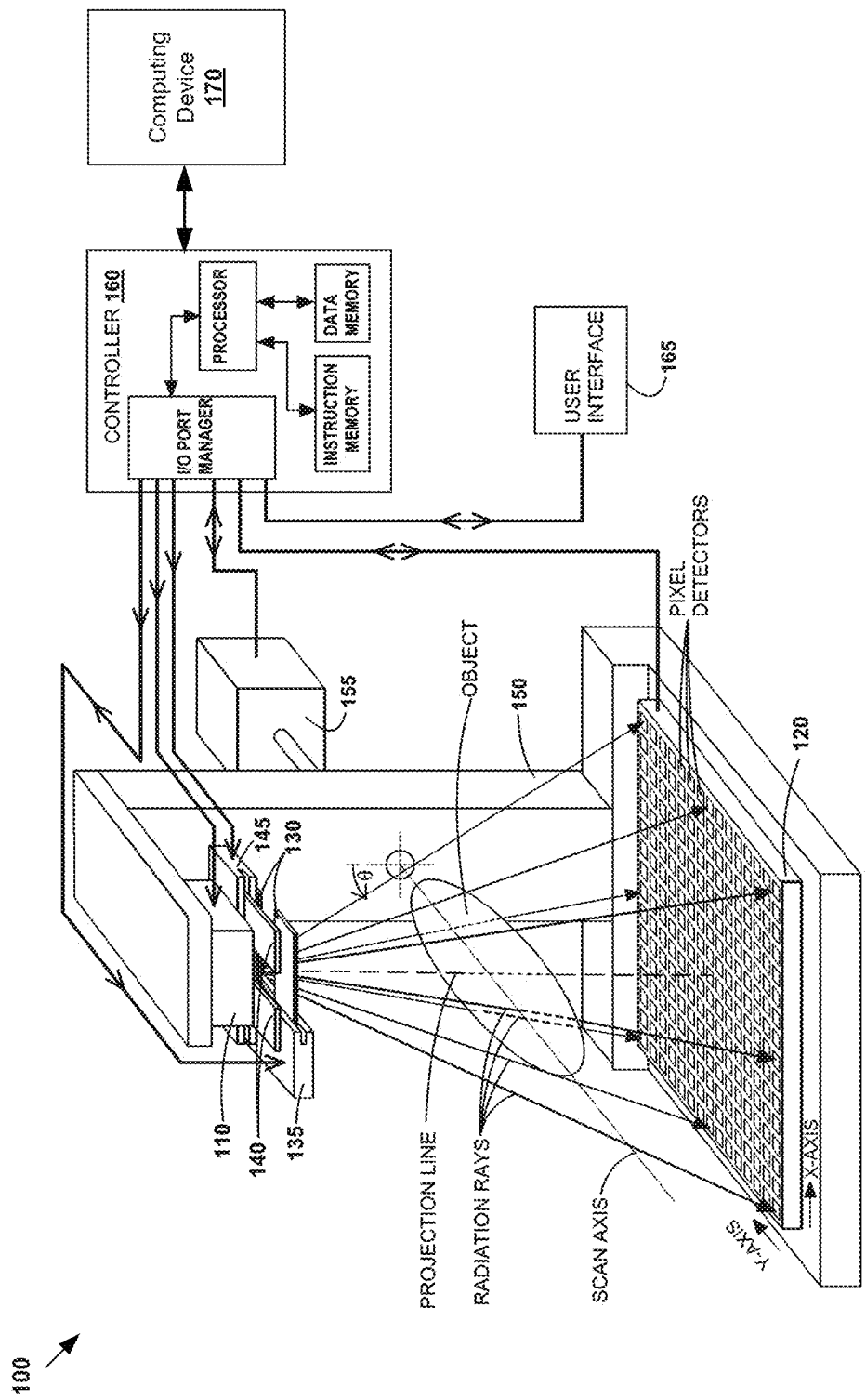
FIG. 1 is an example imaging system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Throughout the present disclosure, the terms "projection view," and "projection angle" are used interchangeably, and "projection," "projection image," and "projection data" are also used interchangeably.

FIG. 1 is an example imaging system 100. The imaging system 100 includes a radiation source 110, a detector 120 having pixel detectors disposed opposite to the radiation source 110 along a projection line, a first set of fan blades 130 disposed between the radiation source 110 and the detector 120, a first fan-blade drive 135 that holds the fan blades 130 and sets their positions. The edges of the fan blades 130 may be oriented substantially perpendicular to the scan axis (defined below), and are substantially parallel with the trans-axial dimension (defined below) of the detector 120.

As an option, the imaging system 100 may further include a second set of fan blades 140 disposed between the radiation source 110 and the detector 120, and a second fan-blade drive 145 that holds the fan blades 140 and sets their positions. The edges of the fan blades 140 may be oriented substantially parallel with the scan axis (defined below), and are substantially perpendicular to the axial dimension (defined below) of the detector 120. The fan blades are generally disposed closer to the radiation source 110 than the detector 120. They are normally kept wide open to enable the full extent of the detector 120 to be exposed to radiation, but may be partially closed in certain situations.

The imaging system 100 further includes a gantry 150 that holds at least the radiation source 110, the detector 120, and the fan-blade drives 135 and 145 in fixed or known spatial relationships to one another, a mechanical drive 155 that rotates the gantry 150 about a target object disposed between the radiation source 110 and the detector 120, with the target object being disposed between the fan blades 130 and 140 on the one hand, and the detector 120 on the other hand. The term gantry has a broad meaning, and covers all configurations of one or more structural members that can hold the above-identified components in fixed or known (but possibly movable) spatial relationships. For the sake of visual simplicity in the figure, the gantry housing, gantry support, and fan-blade support are not shown.

Additionally, the imaging system 100 further includes a controller 160, a user interface 165, and a computing device 170. The controller 160 may be electrically coupled to the radiation source 110, the mechanical drive 155, the fan-blade drives 135 and 145, the detector 120, and the user interface 165. The user interface 165 may be configured to enable a user to at least initiate a scan of the target object, and to collect measured projection data from the detector 120. The user interface 165 may be configured to present graphic representations of the measured data. The computing device 170, coupled to the controller 160, may be configured to perform simulation operations, data processing operations, and other operations.

In the imaging system 100, the gantry 150 may be configured to rotate about the target object during a scan such that the radiation source 110, the fan blades 130 and 140, the fan-blade drives 135 and 145, and the detector 120 circle around the target object. More specifically, the gantry 150 may rotate these components about a scan axis, as shown in FIG. 1, where the scan axis intersects the projection line, and is typically perpendicular to the projection line. The target object is aligned in a substantially fixed relationship to the scan axis. The construction provides a relative rotation between the projection line on the one hand, and the scan axis and a target object aligned thereto on the other hand, with the relative rotation being measured by an angular displacement value θ.

The mechanical drive 155 may be coupled to the gantry 150 to provide rotation upon command by the controller 160. The array of pixel detectors on the detector 120 may be periodically read to obtain the data of the radiographic projections. The detector 120 has an X-axis and a Y-axis, which are perpendicular to each other. The detector 120 may be oriented such that its Y-axis is parallel to the scan axis. For this reason, the Y-axis may also be referred to as the axial dimension of the detector 120, and the X-axis may be referred to as the trans-axial dimension, or lateral dimension, of the device 120.

The X-axis is perpendicular to a plane defined by the scan axis and the projection line, and the Y-axis is parallel to this same plane. Each pixel is assigned a discrete X-coordinate ("X") along the X-axis and a discrete Y-coordinate ("Y") along the Y-axis. A smaller number of pixels are shown in the figure for the sake of visual clarity. The detector may be centered on the projection line to enable full-fan imaging of the target object, may be offset from the projection line to enable half-fan imaging of the target object, or may be movable with respect to the projection line to allow both full-fan and half-fan imaging of target objects.

In a cone-beam system, various components may scatter radiation. Some examples include, without limitation, a bow-tie filter, the object being scanned, an anti-scatter grid, and the detector housing of the system. Additional description is provided in a commonly owned U.S. Pat. No. 8,326,011, which is incorporated by reference herein in its entirety.

Figure 2:
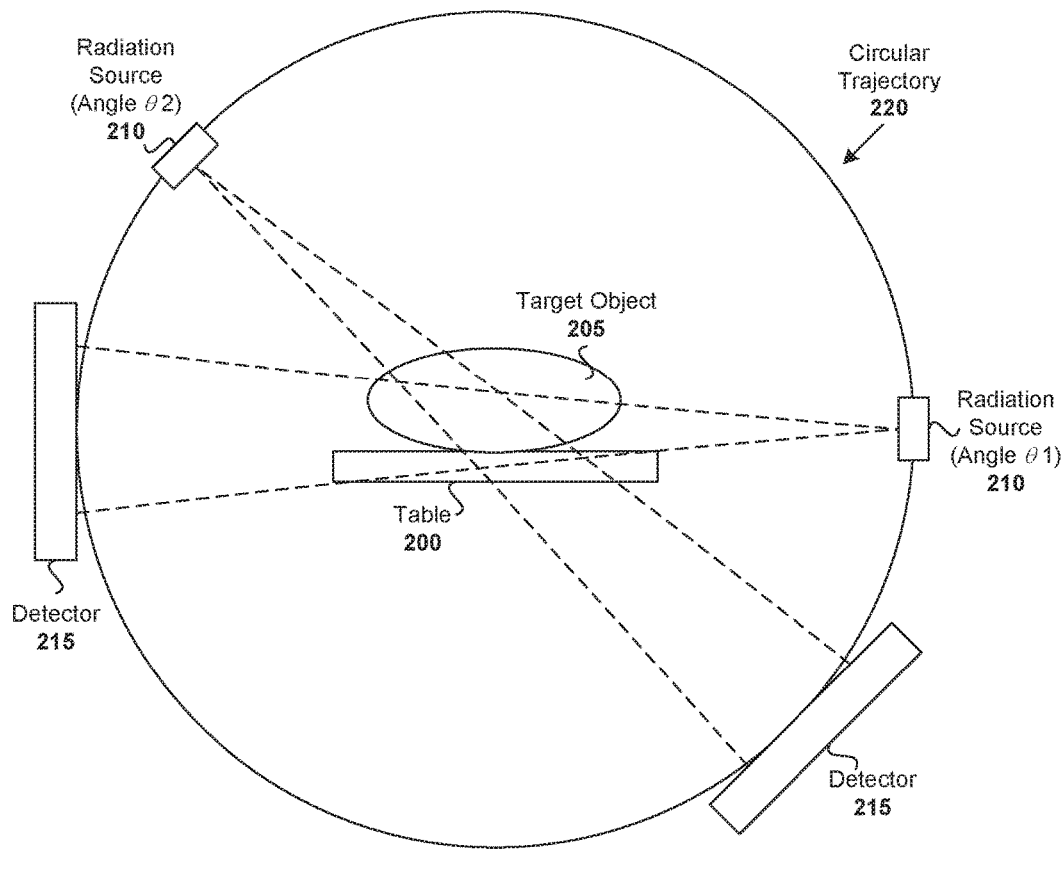
FIG. 2 is an example configuration of a table with respect to a target object on the table, a radiation source, and a detector, for two selected projection angles as provided by rotation of the gantry about the target object along a circular trajectory.

FIG. 2 is an example configuration of a table 200 with respect to a target object 205 on the table 200 (generally a patient, etc.), a radiation source 210, and a detector 215, for two selected projection angles as provided by rotation of the gantry about the target object along a circular trajectory 220. In this example, the X-Y plane is defined as the plane of the paper. The Z axis extends out from the paper. Signals transmitted by the radiation source 210 are also called "primary signals", some of which may pass through the target object 205 and the table 200 before being detected by the detector 215. In addition, due to scattering, the detector 215 also detects scatter signals. The total signals detected by the detector 215 may include both primary signals and scatter signals (also referred to as "primary plus scatter" signals).

While the radiation source 210 may be rotated 360°, and projection data may be generated for every 1°, certain projection data at selected projection angles, such as θ1 and θ2 shown in FIG. 2, may be analyzed and processed differently. For instance, in scatter estimation models, such as the kernel models mentioned above, the set of estimated scatter may be less accurate for certain projection angles, such as, without limitation, in the lateral direction (such as θ1), near approximately 45 degrees (not shown), near approximately 135 degrees (such as θ2). Subsequent paragraphs will further detail how the projection data at such selected projection angles of interest may be processed.

Scatter Estimation

Figure 3:
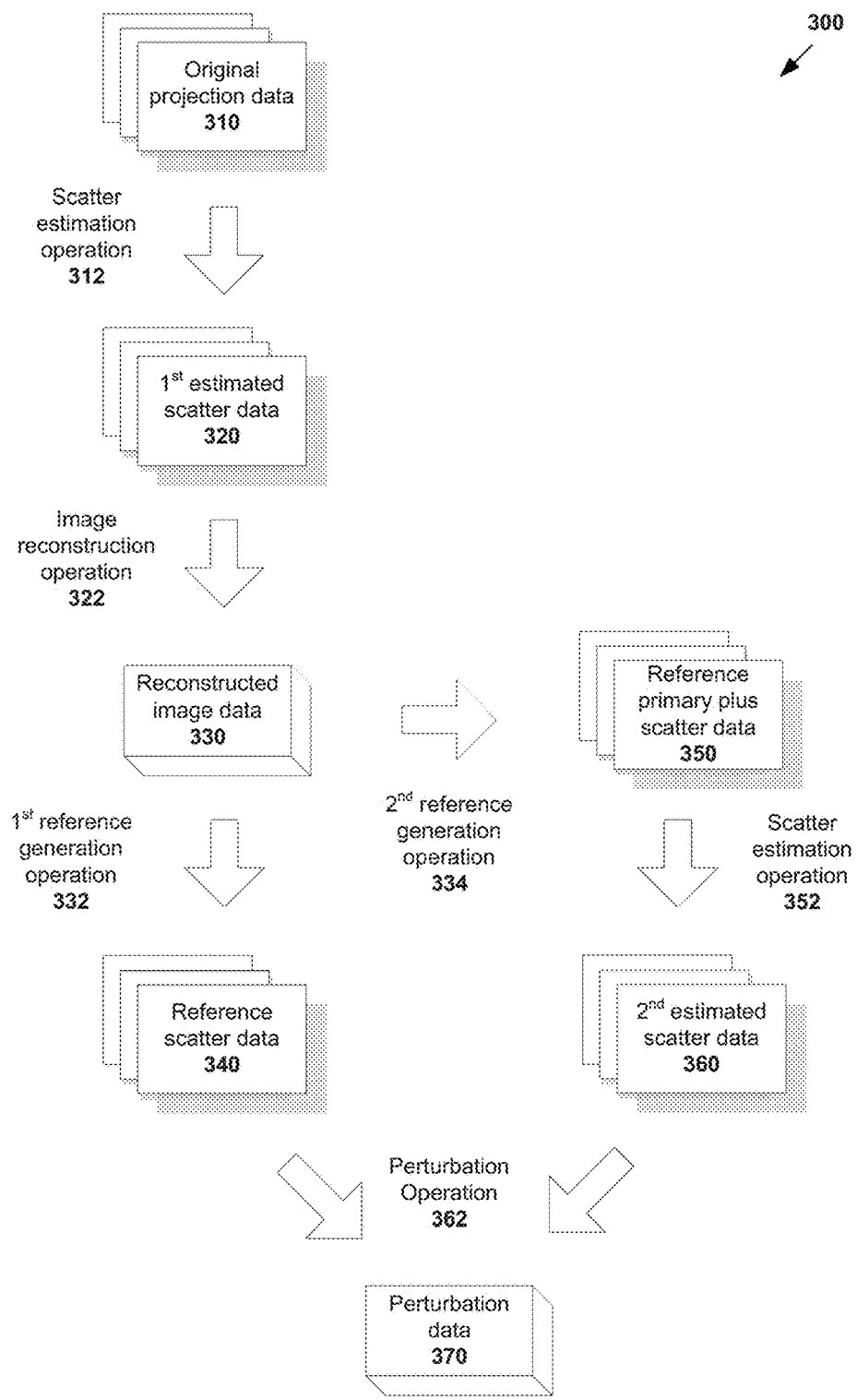
FIG. 3 is an example process flow for scatter estimation associated with a target object.

FIG. 3 is an example process flow 300 for scatter estimation. The example process flow 300 may include one or more operations, functions, or actions illustrated by one or more blocks, such as 310 to 370. The various blocks may be combined into fewer blocks, divided into additional blocks, and/or eliminated based upon the desired implementation. Operations 332 to 362 in FIG. 3 may be performed by the computing device 170 of FIG. 1, or by one or more computing devices not shown in FIG. 1 (e.g., one or more computing devices in a computer cluster).

Referring to 310 in FIG. 3, a set of original projection data 310 that includes primary radiation and scattered radiation at one or more selected projection angles associated with a target object (e.g., a patient) is generated. For example, the radiation source 110 and detector 120 of the imaging system 100 may be used to generate the set of original projections 310 (i.e., raw radiographic projections, also known as "original projections").

Referring to 320 in FIG. 3, a first set of estimated scatter data 320 is generated from the set of original projection data using a scatter estimation algorithm (see scatter estimation operation 312). Any suitable scatter estimation algorithm may be used, such as a kernel-based algorithm, measurement-based technique (e.g., beam stop array, slit scan, detector shadowing technique, etc.).

Referring to 330 in FIG. 3, reconstructed image data 330 is generated by performing a first pass reconstruction using the first set of estimated scatter data 320. Examples image reconstruction operation 322 to generate the reconstructed image data 330 will he explained in more detail with reference to FIG. 4.

Referring to 340 in FIG. 3, a set of reference scatter data 340 associated the target object is generated at the one or more selected projection angles based on the reconstructed image data 330. The set of reference scatter data 340 is associated with scatter signals and may also be referred to as "simulated scatter."

Referring to 350 in FIG. 3, a set of reference primary plus scatter data 350 associated with the target object is generated at the one or more selected projection angles based on the reconstructed image data 330. The set of reference primary plus scatter data 350 is associated with the total signals (i.e., primary plus scatter) detected by a detector (e.g., 120 in FIG. 1 or 215 in FIG. 2) and may also be referred to as "simulated primary+scatter" signals.

It will be appreciated that the set of original projections detected by an imaging system (e.g., detector 120 of system 100) generally includes scatter. By simulating the set of reference scatter data 340 and the set of reference primary plus scatter data 350, scatter may be estimated according to subsequent blocks 360 to 370. A first reference generation operation (see 332) may be used to generate the set of reference scatter data 340, and a second reference generation operation (see 334) to generate the set of reference primary plus scatter data 350. Both operations 332 and 334 will be explained in more detail in conjunction with FIG. 4.

The one or more selected projection angles (see 340 and 350) may be any suitable projection angles that do not necessarily have to coincide with angles of the set of original projections at block 310. For example, the one or more selected projection angles may be certain angles that are known to be undesirable because scatter estimation is generally less accurate at those angles. The one or more selected projection angles may be suitably far apart (using equal or non-equal spacing), such as between 5 and 30 degrees. A blank projection may also be simulated without having an object in the field of view.

Referring to 360 in FIG. 3, a second set of estimated scatter data 360 associated with the target object is generated (e.g., by simulation) based on the set of reference primary plus scatter data 350. For example, the second set of estimated scatter data 360 may be generated using a scatter estimation operation (see 352). Similar to 312, scatter estimation operation 352 may be kernel-based algorithm, measurement-based technique (e.g., beam stop array, slit scan, detector shadowing technique, etc.), and others.

Referring to 370 in FIG. 3, perturbation data 370 associated with the target object is generated based on the set of reference scatter data 340 and the second set of estimated scatter data 360. The perturbation data 370 represents the scatter correction required (e.g., the amount that may need to be adjusted, where this amount may correspond to the differences between the set of estimated and the simulated scatter).

The perturbation data 370 may be generated using a perturbation operation (see 362) that is non-parametric, parametric, or a combination of both. In practice, the perturbation data 370 may be a two-dimensional (2D) perturbation map. The generation of the perturbation data 370 will be explained in further detail in conjunction with FIG. 5.

Using the perturbation data 370, the first set of estimated scatter data 320 may be re-applied to the set of original projections 310, and the first set of estimated scatter data 320 perturbed using the perturbation map to generate a refined set of estimated scatter data (not shown for simplicity). The set of original projections 310 may then be corrected using the refined set of estimated scatter data, and then reconstructed.

According to the examples in FIG. 3, the second set of estimated scatter data 360 is generated based on the set of reference primary plus scatter data 350. This in turn allows the perturbation data 370 to be generated by comparing the second set of estimated scatter data 360 and the set of reference scatter data 340, instead of relying on a comparison between estimated scatter from the set of original projections with the set of reference scatter data. In at least some examples, this approach eliminates the need to address the difficult process of scaling the set of reference scatter data 340 (representing the simulation profile) to match, for example, measured scatter data. In addition, this approach may also be more tolerant to projection angle and/or phantom model mismatches, because this approach may focus on identifying errors that are rooted in the scatter estimation method in use. This also allows simulation and modelling of any other scattering sources present in an imaging system in practice.

Reference Data Generation

Figure 4:
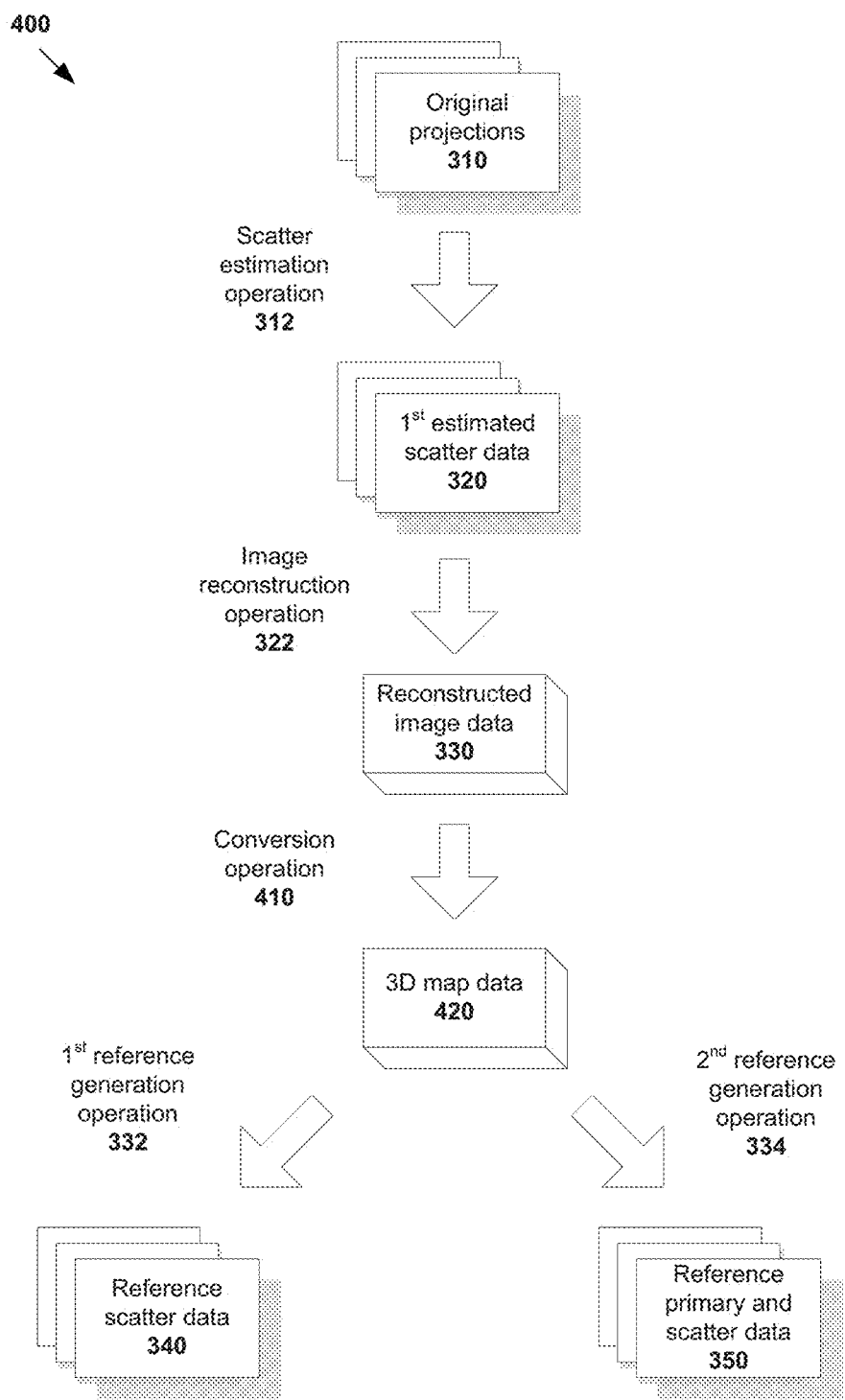
FIG. 4 is an example process flow for generating a set of reference scatter data and a set of reference primary plus scatter data.

FIG. 4 is an example process flow 400 for generating the set of reference scatter data 340 and the set of reference primary plus scatter data 350 in FIG. 3. The example process flow 400 may include one or more operations, functions, or actions illustrated by one or more blocks, such as 310 to 350 and 410 to 420. The various blocks may be combined into fewer blocks, divided into additional blocks, and/or eliminated based upon the desired implementation.

As explained with reference to FIG. 3, the first set of estimated scatter data 320 may be generated from the set of original projection data 310 using any suitable scatter estimation algorithm (e.g., kernel-based, measurement-based, etc.). Although not shown, a set of corrected projections may first be generated from the set of original projections 310. For example, this may involve applying a correction operation (e.g., scatter kernel superposition, etc.) on the set of original projections 310 to make corrections for scatter, beam-hardening, etc.

Referring to 330 and 332 in FIG. 4, reconstructed image data 330 associated with the target object is generated based on the set of corrected projections 310. For example, this may involve performing an image reconstruction operation 322, such as a first-pass cone beam computed tomography (CBCT) reconstruction. The reconstructed image data 330 may be in the form of Hounsfield Units (HUs) representation, and known as a volumetric image, image volume, etc.

Referring to 410 and 420 in FIG. 4, the reconstructed image data 330 is converted to 3D map data 420, such as by performing a conversion operation 410. The 3D map data 420 generally contains appropriate material compositions and densities resembling the target object being image (e.g., bone structures, certain organs, etc.). Also, the 3D map data 420 may be used to model x-ray transport using Monte Carlo simulations or other techniques. In one example, the conversion operation 410 may include the following:

(i) The reconstructed image data 330 may be first down-sampled to reduce its matrix size, such as by binning the original voxels into larger ones (e.g., to 1×1×1 cm voxels, etc.).

(ii) The down-sampled reconstructed image data 330 may then be extended in the axial direction (the cone angle direction, along the axis of rotation) to avoid (or reduce) truncation artifacts, and to simulate the presence of scattering media outside the cone beam as necessary.

(iii) If a known object (e.g., the patient table) is truncated or not in the field of view (FOV), then the known truncated object can be inserted back into the down-sampled reconstructed image data 330.

(iv) Image intensities of the down-sampled reconstructed image data 330 may be converted into different material types and densities using segmentation algorithms or a single material with different densities.

Referring to 332 in FIG. 4, the set of reference scatter data 340 is generated based on the 3D map data 420, such as by performing the first reference generation operation 332 to simulate scatter signals at one or more selected projection angles.

Referring to 334 in FIG. 4, the set of reference primary plus scatter data 350 is generated based on the 3D map data 420, such as using the second reference generation operation 334 to simulate primary plus scatter signals at one or more selected projection angles. For example, primary plus scatter signals in a specific number of radiographic projections associated with a specific number of view angles may be simulated.

The first reference generation operation 332, or second reference generation operation 334, or both, may include performing Monte Carlo simulations or deterministic computations based on the reconstructed image data 330 or 3D map data 420.

In more detail, any suitable generation operation 332/334 may be used. For example, Monte Carlo simulations may be performed on a selected subset of pixel detectors of a detector (e.g., selected rows of the pixel detectors, see also 120 in FIG. 1) and/or projection views at projection angles that may be known to yield undesirable scatter estimates to generate the set of reference scatter data 340. Additionally or alternatively, a deterministic method (e.g., by solving equations) may be used. For example, deterministic particle transport equations such as Boltzmann Transport equations may be solved using a Boltzmann solver. In yet another example, scatter measuring techniques, such as, without limitation, the beam blocker method, modulation method, slit scan method, and collimator shadowing technique may be utilized to obtain the reference scatter data. In one implementation of the collimator shadowing technique, a portion of the detector 120, typically in one or more of its edges, may be blocked from a primary signal by the fan blades 130 or additional such devices. The reference generation operations 332/334 may also be based on any combination of x-ray beam spectrum, imaging geometry and imaging components (e.g., bowtie filter and anti-scatter grid. etc.) of the imaging system (e.g., 100 in FIG. 1), the reconstructed image data 420 and the 3D map data 420.

In the example in FIG. 4, it is possible, in order to reduce the influence of any image artifacts on the set of reference scatter data 340, to apply certain image processing techniques on the to reduce or remove those artifacts prior to the conversion operation 410. An example of possible processing operations is the de-streaking technique that is described in the U.S. patent application Ser. No. 13/154,465. It is also possible to perform the conversion operation 410 first to generate the 3D map data 420, followed by the down-sampling operation. The down-sampling operation may also be realized by methods other than the simple binning method mentioned here, for example those commonly known to a person skilled in the art.

Although various examples have been described with reference to FIG. 4, it should also be noted that for the first-pass reconstruction, one can use the best possible correction, or instead focus on speed without any correction, and/or use only a subset of the original projections 310, or anything in between. Alternatively, one may use a prior scan, such as a planning CT in radiation therapy, for example, for scatter simulation and calculation, avoiding the need of the first-pass reconstructions.

Perturbation Data Generation

Figure 5:
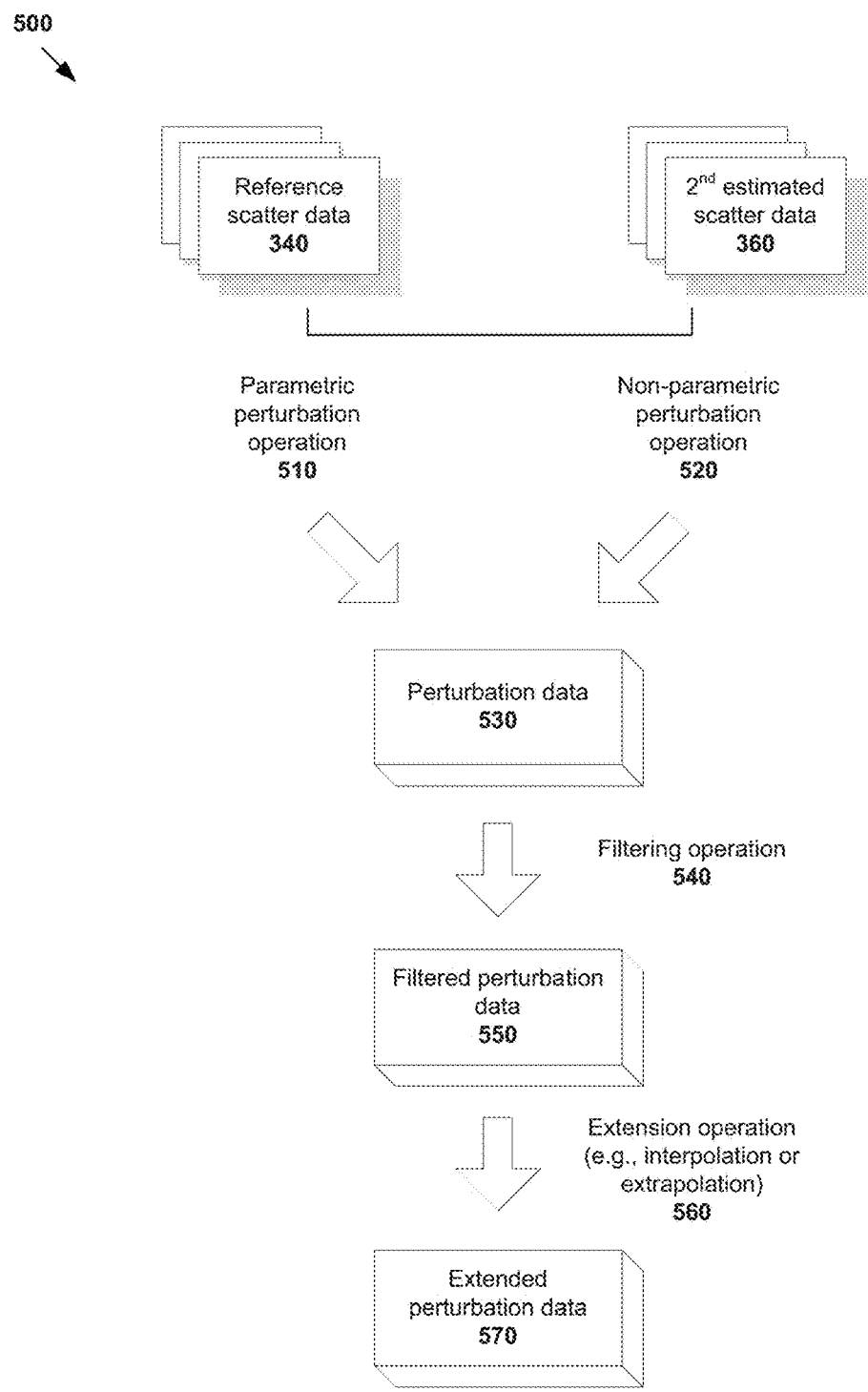
FIG. 5 is an example process flow for generating perturbation data.

FIG. 5 is an example process flow 500 for generating the perturbation data 370 in FIG. 3. The example process flow 500 (related to perturbation operation 362 in FIG. 3) may include one or more operations, functions, or actions illustrated by one or more blocks, such as 510 to 570. The various blocks may be combined into fewer blocks, divided into additional blocks, and/or eliminated based upon the desired implementation.

Referring to 510 to 520 in FIG. 5, any suitable approach may be used to generate perturbation data 530, such as either or both of the following:

(a) A parametric perturbation operation 510 may be performed to optimize one or more kernel parameters of a kernel model. The parameters of interest may be any suitable parameters, such as kernel amplitude, kernel width and asymmetry factor, etc. The parameters may also be related to object scatter, anti-scatter grid, detector scatter, and any parameters employed by scatter kernel superposition methods. The optimization may include defining and optimizing a goal function. In general, "parametric perturbation" may refer to a method of perturbing scatter estimates by solving for the scatter kernel parameters (based on some scatter references either from measurements or a simulation or calculation, such as Monte Carlo simulation or deterministic calculation). The perturbation to scatter is done through the changes in the scatter kernel parameters.

(b) A non-parametric perturbation operation 520 may be performed, such as subtraction, division, etc. In contrast to parametric perturbation, "non-parametric perturbation" refers to perturbing the scatter estimates directly without first modifying the kernel parameters. By using such a non-parameterized approach, it is not necessary to perform an optimization to find the best parameters for perturbation, and more complicated perturbation data may be accommodated.

The non-parametric perturbation operation 520 may include comparing the set of reference scatter data 340 with the second set of estimated scatter data 360. Based on the comparison, a perturbation factor may be determined as a function of pixel location for each of the one or more selected projection angles. For example, the perturbation factor may be a ratio between the simulated ground truth scatter (e.g., the set of reference scatter data 340) and the second set of estimated scatter (e.g., 360). The perturbation factor may be derived as a function of pixel location for each of the one or more selected projection angles of the set of reference scatter data 340 or reference primary plus scatter data 350. The perturbation data 540 may be in the form of 2D map that represents the scatter correction required.

It will be appreciated that the perturbation data 530 may be the parametric operation 510, the non-parametric operation 520, or a combination of both. For example, the parametric operation 510 may be used to optimize one or more scatter kernel parameters of a kernel model. Any residual errors may be accounted for using the non-parametric operation 520.

Referring to 540 to 570 in FIG. 5, one or more operations may be performed on the perturbation data 530, such as to reduce noise and to extend to all projection angles. It will be appreciated that the perturbation data 370 illustrated in FIG. 3 may be 530, 550 or 570 in FIG. 5. The operations will be described in more detail below.

In one example, a filtering operation 540 may be performed for reduce noise of and smoothing the perturbation data 530. This is to address the potential for noise to be introduced into the perturbation data 530, such as when the non-parametric perturbation operation 520 is used. Additionally, or alternatively, simulation results (e.g., the set of reference scatter data 340 or reference primary plus scatter data 360) may be filtered. After filtering, the perturbation data 530 may he referred to as filtered perturbation data 550.

In another example, an extension operation 560 may be performed to extend the perturbation data 550 to all projection angles via interpolation and/or extrapolation. When the non-parametric perturbation operation 520 is used, interpolation or extrapolation is performed on the (non-parametric) perturbation data 550. This approach is generally more robust than interpolating or extrapolating parameters in the case of parametric perturbation operation 510. Also, a parameter interpolation is 1-D interpolation, while the non-parametric 2D perturbation map may be spatially better defined and more specific. As such, the non-parametric perturbation operation 520 may be used to improve accuracy and reduce overall errors since any local errors will affect only a small portion of the detector pixels.

There are many ways of performing the extension operation 560 using interpolation and/or extrapolation. Some examples include, without limitation, non-linear interpolation, operations employing a second order polynomial, cubic spline interpolation, etc. The view number and projection angle at the end of a scan may need to be taken into account in calculations. For example, when the scan is not 360 degrees, extrapolation operation may be needed in addition to interpolation.

Although some examples are described above, it should be noted that scatter correction using a non-parametric perturbation may be performed differently than in the application where just the scatter parameters were modified. Here, scatter may be first estimated using the kernel method, and then the estimate may be modified by the perturbation data. It should also be noted that the set of reference scatter calculation (see 332 in FIG. 4) may also be obtained with scatter measurement techniques such as the beam blocker, primary modulator, slit scan, or collimator shadowing technique. In one embodiment, the perturbation data may be derived on a portion of the detector for each projection, thus requires interpolation or extrapolation within each projection but no interpolation over projection angle. Scatter may be generated on a subset of detector pixels (e.g., using Monte Carlo simulations, or deterministic calculations, or both), and the perturbation may be derived over just a portion of the detector.

Example Implementation

Figure 6:
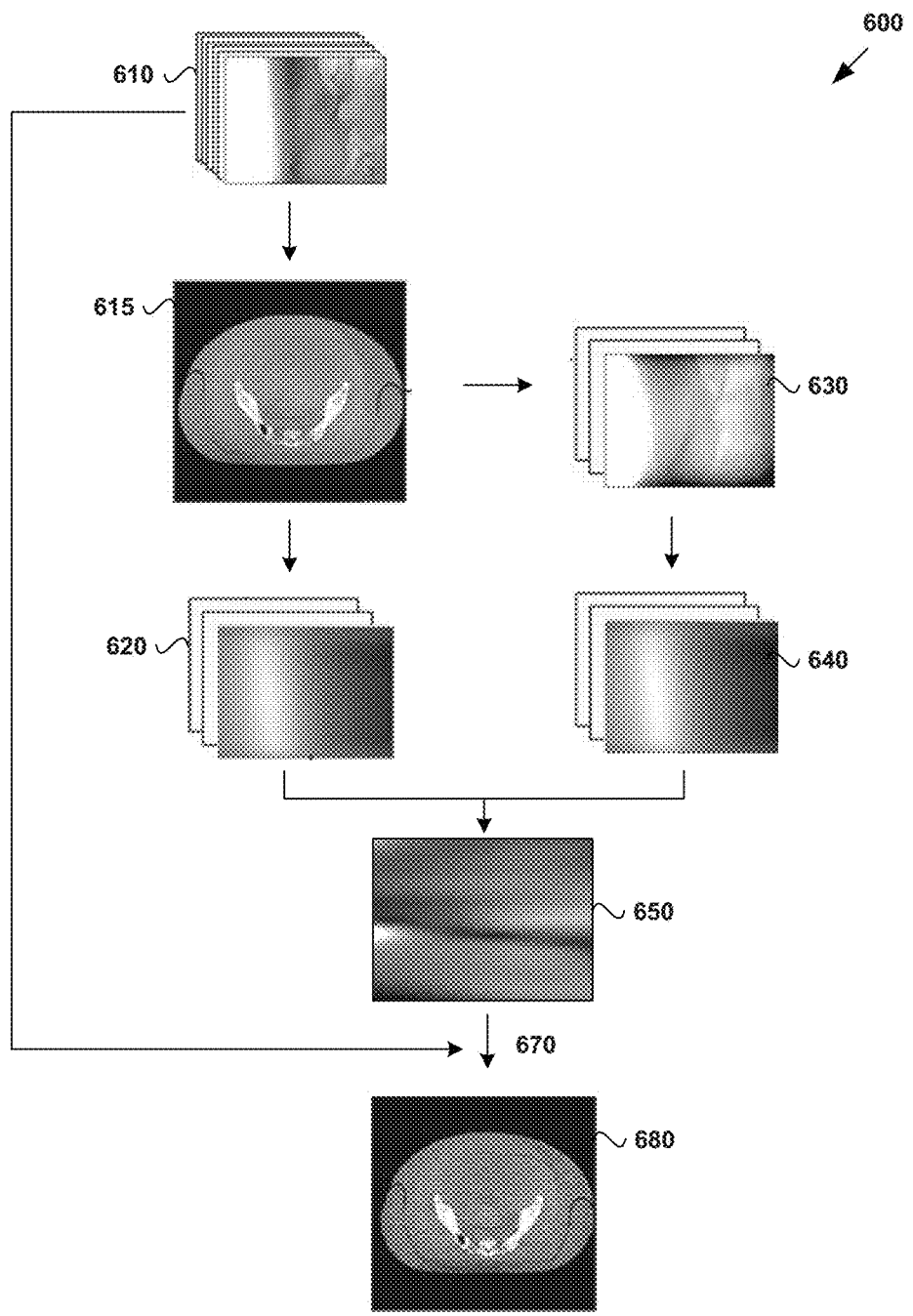
FIG. 6 is an example implementation of scatter estimation associated with a target object according to the example process flow in FIG. 3.

FIG. 6 is an example implementation of scatter estimation associated with a target object according to the example process flow in FIG. 3. In this example, the target object is a patient, and more particularly, a pelvic area of the patient. A two-pass reconstruction process may be used to generate high quality CBCT images. In summary, a refined scatter estimate, based on the first-pass reconstruction, may be applied to generate an improved second pass estimate. The refined estimate may be obtained through Monte Carlo (or other) simulations of x-ray transport through the first-pass reconstruction.

Referring to 610 in FIG. 6 (related to 310 in FIG. 3), a set of original projections associated with the target object is generated in a first operation. Next (related to 320 in FIG. 3), the set of original projections is reconstructed to generate reconstructed image data 615. The reconstructed image data 615 may then be converted to a 3D map containing appropriate material compositions and densities. From the reconstructed image data 615 or 3D map, a set of reference scatter data 620 (related to 340 in FIG. 3) and a set of reference primary plus scatter data 630 (related to 350 in FIG. 3) may then be generated. A second set of estimated scatter data 640 (related to 360 in FIG. 3) may then be generated from the set of reference primary plus scatter data 630.

Next, perturbation data 650 (related to 370 in FIG. 3) may be generated based on the set of reference scatter data 620 and the second set of estimated scatter data 640, such as according to the non-parametric approach, parametric approach, or both, described with reference to FIG. 5. The extension operation 560 in FIG. 5 may be performed to extend the perturbation data 650 to all projection angles.

Figure 7:
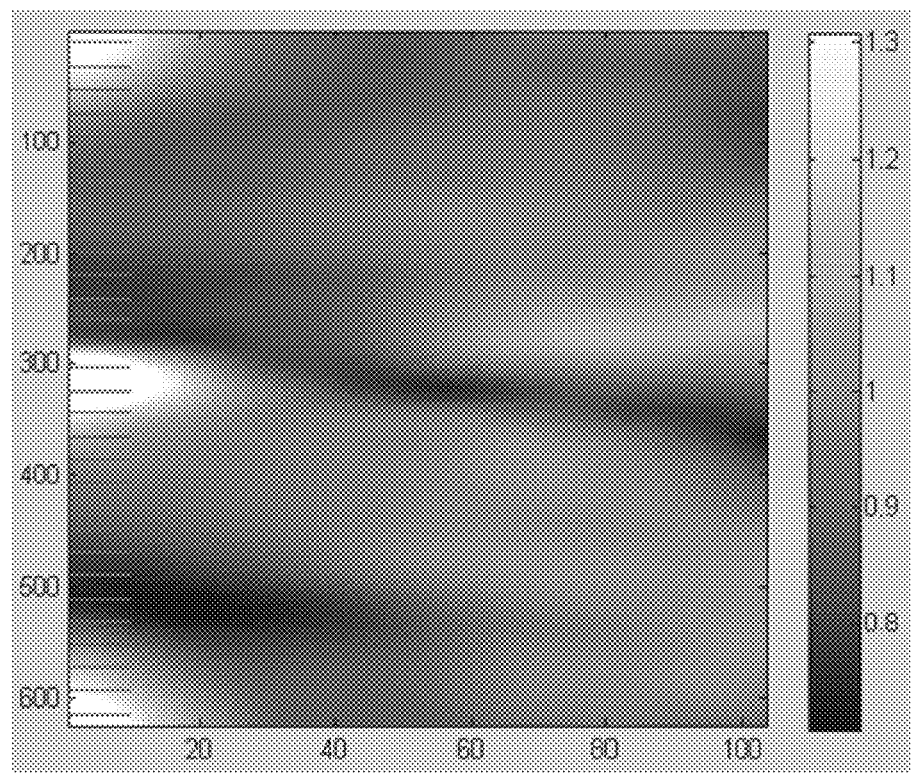
FIG. 7 is an example sinogram perturbation map.

In more detail, FIG. 7 is an example sinogram perturbation map formed from the central detector row(s) of each projection associated with a large pelvis phantom. The x-axis represents detector superpixels (e.g., down-sampled detector pixels), and the y-axis is the projection number. The marker bars indicate those projections that were simulated at the one or more selected projection angles described above. The values ranging from 0.7 and 1.3 shown in FIG. 7 represent the perturbation values in the perturbation map. This map may be used to modify the first set of estimated scatter data (see 320 in FIG. 3) to generate a set of refined estimated scatter. For example, a perturbation value of 1 for a pixel means that no refinement is necessary for that pixel. A perturbation value of 1.3, on the other hand, means that a corresponding pixel in the first set of estimated scatter data 320 is multiplied by 1.3.

Referring to 670 in FIG. 6, the first set of estimated scatter data (see 320 in FIG. 3) may then be reapplied to the set of original projections 610 (or from previously saved results), and refined to generate a refined set of estimated scatter data by perturbing the first set of estimated scatter data 320 using the perturbation data 650. The set of original projections 610 may then be corrected with the refined set of estimated scatter data and reconstructed into a final image (see 680 in FIG. 6).

FIG. 8A, FIG. 8B, FIG. 80 and FIG. 8D are reconstructed images of a large pelvis phantom scanned using an imaging system (e.g., CBCT system). In the examples shown, the perturbation data 650 is generated using the non-parametric perturbation operation (see 520 in FIG. 5) described above. FIG. 8A and FIG. 8B show what can be achieved with scatter kernel superposition method, while FIG. 8C and FIG. 8D show the improvements attained using the non-parametric perturbation. FIG. 8B and FIG. 8D are the difference images with respect to a ground truth reference image. With perturbation, image uniformity is improved and the root-mean-square (RMS) error is reduced from 26 Hounsfield unit (HU) in FIG. 8B to 16 HU in FIG. 8O.

Example Computing Device

Figure 9:
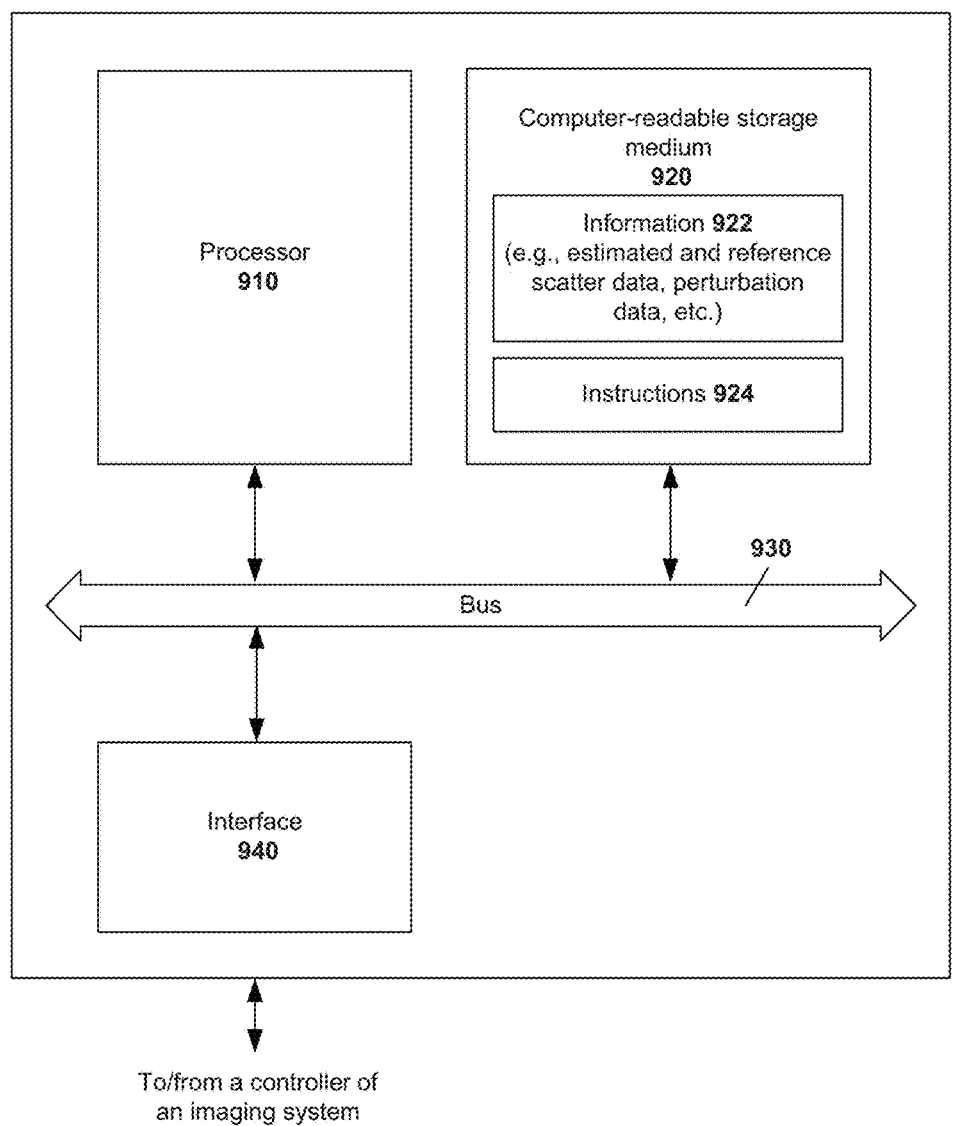
FIG. 9 is an example computing device that may be configured to perform scatter estimation.

The above examples can be implemented by hardware, software or firmware or a combination thereof. FIG. 9 is a schematic diagram of an example computing device 900 for estimating scatter. Example computer system 900 may include processor 910, computer-readable storage medium 920, interface 940 to interface with an imaging system (e.g., 100 in FIG. 1), and bus 930 that facilitates communication among these illustrated components and other components. Processor 910 is to perform processes described herein with reference to FIG. 1 to FIG. 8D.

Computer-readable storage medium 920 may store any suitable information 922, such as information relating to a set of original projections, a set of reference scatter data, a set of reference primary plus scatter data, a set of estimated scatter data, reconstructed image data, perturbation data, etc. Computer-readable storage medium 920 may further store computer-readable instructions 924 which, in response to execution by processor 910, cause processor 910 to perform processes described herein with reference to FIG. 1 to FIG. 8D.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

We claim:

1. A method for a computing device to estimate scatter associated with a target object, comprising:
   the computing device generating a first set of estimated scatter data from a set of original projection data using a scatter estimation algorithm, wherein the set of original projection data is acquired using a radiation source and a detector of an imaging system, and the set of original projection data includes primary radiation and scattered radiation at one or more selected projection angles associated with the target object;
   the computing device generating reconstructed image data by performing a first pass reconstruction using the first set of estimated scatter data;
   the computing device generating a set of reference scatter data associated with the target object at the one or more selected projection angles based on the reconstructed image data;
   the computing device generating a set of reference primary plus scatter data associated with the target object at the one or more selected projection angles based on the reconstructed image data;
   the computing device generating a second set of estimated scatter data associated with the target object based on the set of reference primary plus scatter data using the scatter estimation algorithm; and
   the computing device generating perturbation data associated with the target object by performing a non-parametric perturbation operation to compare the reference scatter data with the second set of estimated scatter data.

2. The method of claim 1, wherein the scatter estimation algorithm is a kernel-based algorithm.

3. The method of claim 2, wherein the one or more scatter kernel parameters of a kernel model in the kernel-based algorithm include at least one of: kernel amplitude, kernel width or asymmetry factor.

4. The method of claim 1, wherein the scatter estimation algorithm is a measurement-based technique using beam stop array, slit scan or detector shadowing technique.

5. The method of claim 1, wherein generating the set of reference primary plus scatter data or generating the set of reference scatter data comprises:
   performing Monte Carlo simulations on the reconstructed image data.

6. The method of claim 1, wherein generating the set of reference primary plus scatter data or generating the set of reference scatter data comprises:
   performing deterministic computations based on the reconstructed image data.

7. The method of claim 1, wherein generating the perturbation data comprises:
   based on the comparison, determining a perturbation factor associated with each of the one or more selected projection angles, wherein the perturbation data is in the form of a perturbation map.

8. The method of claim 1, wherein the non-parametric perturbation operation includes at least one of: subtraction or division between the set of reference scatter data and the second set of estimated scatter data.

9. The method of claim 1, wherein generating the perturbation data comprises:
   extending the perturbation data, which is generated based on the set of reference scatter data and the second set of estimated scatter data at the one or more selected projection angles, for all original projection angles via interpolation or extrapolation.

10. The method of claim 9, further comprising:
    generating a refined set of estimated scatter data associated with the target object by adjusting the first set of estimated scatter data based on the extended perturbation data.

11. The method of claim 10, further comprising:
    adjusting the set of original projections based on the refined set of estimated scatter data; and
    generating refined reconstructed image data associated with the target object based on the adjusted set of original projections.

12. An imaging system configured to estimate scatter associated with a target object, comprising:
    a radiation source;

a detector; and a computing device, wherein the radiation source and the detector are configured to acquire a set of original projection data that includes primary radiation and scattered radiation at one or more selected projection angles associated with the target object, and the computing device is configured to:

- generate a first set of estimated scatter data from the set of original projection data using a scatter estimation algorithm;
- generate reconstructed image data by performing a first pass reconstruction using the first set of estimated scatter data;
- generate a set of reference scatter data associated with the target object at the one or more selected projection angles based on the reconstructed image data;
- generate a set of reference primary plus scatter data associated with the target object at the one or more selected projection angles based on the reconstructed image data;
- generate a second set of estimated scatter data associated with the target object based on the set of reference primary plus scatter data using the scatter estimation algorithm; and
- generate perturbation data associated with the target object by performing a non-parametric perturbation operation to compare the reference scatter data with the second set of estimated scatter data.

13. The imaging system of claim 12, wherein the scatter estimation algorithm is a kernel-based algorithm.

14. The imaging system of claim 13, wherein the one or more scatter kernel parameters of a kernel model in the kernel-based algorithm include at least one of: kernel amplitude, kernel width or asymmetry factor.

15. The imaging system of claim 12, wherein the scatter estimation algorithm is a measurement based technique using beam stop array, slit scan or detector shadowing technique.

16. The imaging system of claim 12, wherein the computing device is configured to generate the set of reference primary plus scatter data or the set of reference scatter data by performing one of the following:

Monte Carlo simulations on the reconstructed image data, deterministic computations based on the reconstructed image data.

17. The imaging system of claim 12, wherein the computing device is configured to generate the perturbation data by:

based on the comparison, determining a perturbation factor associated with each of the one or more selected projection angles, wherein the perturbation data is in the form of a perturbation map.

18. The imaging system of claim 12, wherein the non-parametric perturbation operation includes at least one of: subtraction or division between the set of reference scatter data and the second set of estimated scatter data.

19. The imaging system of claim 12, wherein the computing device is configured to generate the perturbation data by:

extending the perturbation data, which is generated by comparing the set of reference scatter data with the second set of estimated scatter data at the one or more selected projection angles, for all original projection angles via interpolation or extrapolation.

20. The imaging system of claim 19, wherein the computing device is further configured to:

generate a refined set of estimated scatter data associated with the target object by adjusting the first set of estimated scatter data based on the extended perturbation data;

adjust the set of original projections based on the refined set of estimated scatter data; and generate refined reconstructed image data associated with the target object based on the adjusted set of original projections.

* * * * *